United States Patent [19]

Tanghøj

[11] Patent Number: 5,669,893
[45] Date of Patent: Sep. 23, 1997

[54] EXTERNAL URINARY CATHETER

[75] Inventor: Allan Tanghøj, Frederiksberg, Denmark

[73] Assignee: Coloplast A/S, Denmark

[21] Appl. No.: 569,192

[22] PCT Filed: Jun. 29, 1994

[86] PCT No.: PCT/DK94/00268

§ 371 Date: Dec. 29, 1995

§ 102(e) Date: Dec. 29, 1995

[87] PCT Pub. No.: WO95/01144

PCT Pub. Date: Jan. 12, 1995

[30] Foreign Application Priority Data

Jul. 2, 1993 [DK] Denmark .................. 0793/93

[51] Int. Cl.[6] ........................................ A61F 5/44
[52] U.S. Cl. ................................ 604/349; 604/352
[58] Field of Search ........................ 604/349–352

[56] References Cited

U.S. PATENT DOCUMENTS 4,388,923  6/1983  Heimreid .................. 604/352

FOREIGN PATENT DOCUMENTS 520401   2/1931  Germany ................... 604/349
2126483  3/1984  United Kingdom ......... 604/352

Primary Examiner—Robert A. Clarke
Attorney, Agent, or Firm—Ostrolenk, Faber, Gerb & Soffen, LLP

[57] ABSTRACT

An external urinary catheter for the mild of male urinary incontinence comprises an inner catheter member (1) to be placed under the foreskin (3) in abutment with the head (glans) (4) of penis and an outer holder member (10) for fastening the inner catheter member (1) in the state of use. The outer holder member (10) is a separate member enveloping the discharge spout (2), but may be displaced axially in relation thereto.

13 Claims, 1 Drawing Sheet

EXTERNAL URINARY CATHETER

BACKGROUND OF THE INVENTION

The invention relates to an external urinary catheter for the relief of male urinary incontinence comprising an inner catheter member with a tubular discharge spout for connection with a hose, said catheter member being arrangeable, in use, in a position under the foreskin of a penis in surface contact with the head (glans) thereof, and a separate outer holder member for circumferential engagement with the external side of the foreskin to maintain the inner catheter member in said position.

For the relief of male urinary incontinence, external catheters are generally used in the form of condomlike tubular sheaths to be placed externally on penis and having a discharge spout which via a hose is connected with a urine collection bag.

Such external catheters are known in numerous designs and in many cases serve as a satisfactory solution of male incontinence problems. The complete envelopment of penis may, however, give rise to troubles, partly because the application which is effected by unrolling the catheter requires a certain length of penis, partly in use due to the fact that the envelopment of the full length of penis with the catheter which is generally fastened adhesively either by means of a separate adhesive strip or by means of an internal adhesive layer involves strain of the skin and the constantly humid environment from the delivered urine entail skin problems, Such as allergy and maceration and in worst case ulceration.

The application problem entails that conventional external catheters cannot be used by incontinence patients having a too small or retracted penis.

Published patent application GB-A-2075847 proposes an external male urinary catheter in the form of a relatively short funnel-like uridom device which is placed directly against glans penis throughout its length, but nevertheless envelops glans and is kept in place under the foreskin. Around a discharge spout of the device, an external sheath is fastened which after the application of the catheter is brought in abutment with the outer side of the foreskin so that the whole device is kept in place by the position of the foreskin between the inner catheter element and the external sheath.

As conventional catheters of the above-mentioned kind, said prior art urinary catheter requires a relatively accurate adaptation to the anatomy of the user and must thus, inter alia, be manufactured in various sizes. The manufacturing which may be effected by injection moulding is further complicated by the integrated design of the inner catheter member and the outer holder member. The complete envelopment of glans penis with the inner catheter member, whereby the proximal end edge thereof which is provided with a bead is placed against the relatively sensitive skin band between glans and foreskin, may in use give rise to considerable nuisance. Furthermore, the fixation principle requires that the outer holder member during application is rolled onto the outer side of the foreskin. In spite of this, there may be a risk that the catheter might fall off in use in the case of a pull, e.g. from the collection bag connected with the discharge spout, or compressive load from the delivered urine.

GB-A-2 126 483 discloses a urine ducting device in the form of a tubular member, e.g. of silicone rubber, which in use is arranged outside the glans in extension thereof, so that a rather severe extension of the foreskin is required to keep the tubular member in place by the arrangement of an adhesive strip or a strap member sandwiched between adhesive strips on the external side of the foreskin.

This device has thus a structure which would result in considerable discomfort to the user.

SUMMARY OF THE INVENTION

On the basis of said prior art it is the object of the invention to provide an external urinary catheter which through a further development of the fastening concept explained in the above GB patent application entails an easier application and appreciably improved use properties as regards a more secure fastening and reduced inconveniences in fastening the inner catheter member about the mouth of urethra. It is further an object to provide a product design which is more simple to manufacture.

The urinary catheter according to the invention is for this purpose characterized in that the inner catheter member has a short axial length of 5 to 35 mm so as to cover, in said position, the extreme portion of glans outside the point where glans has its largest diameter, the outer holder member comprising a tubular spout part for axially displaceable arrangement around the discharge spout of the inner catheter member to permit axial displacement of the holder member towards a position of use in which a part of the holder member integrally connected the tubular spout part engages at least part of the external side of the foreskin opposite the underlying inner catheter member.

In relation to the prior art catheter according to above GB patent application, the design of the outer holder member with a tubular spout part which is placed on the discharge spout of the inner catheter member and which after arrangement of the inner catheter member under the foreskin is axially displaced to press the holder member into engagement with the outer side of the extreme portion of the foreskin, has shown to entail a particularly reliable fastening with no substantial inconveniences to the user, since a load in the form of a pull at the discharge spout, e.g. due to the weight of the urine collection bas connected with the discharge spout, or a compressive load in connection with the urination, instead of involving the risk that the catheter falls off, entails an improvement of the fastening of the foreskin between the inner catheter member and the outer holder member.

A preferred embodiment of the invention is characterized in that the inner catheter member has such a short axial extent that in use it only covers the extreme portion of glans outside the point where glans has its largest diameter, and in that said inner catheter member in the area at the transition to the discharge spout is formed with such a form stability that its outer shape is preserved at the place where it is fastened by the foreskin.

In relation to the prior art catheter according to above GB patent application, there is thereby obtained a substantially less disturbing position without the risk of tissue damage as a result of that only the extreme portion of glans is covered by the inner catheter member.

Thereby, the possibility is further obtained that the catheter according to the invention may be manufactured as a "one-size" product, which considerably reduces the cost of storage and thus makes the production less expensive.

The improved form stability in the area at the transition to the discharge spout entails that the catheter member through a suitable outer shape may be produced with an improved security against falling off in use due to a pull or compressive load.

DESCRIPTION OF THE INVENTION

Figure 1:
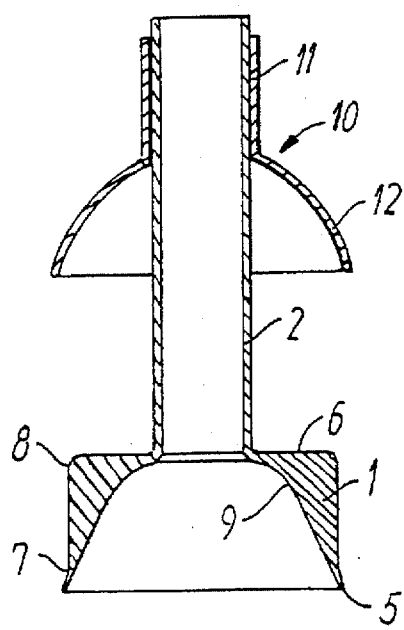
FIG. 1 shows a sectional view of a preferred embodiment of the catheter according to the invention, FIG. 2 the catheter shown in FIG. 1 in an applied condition.
Figure 2:
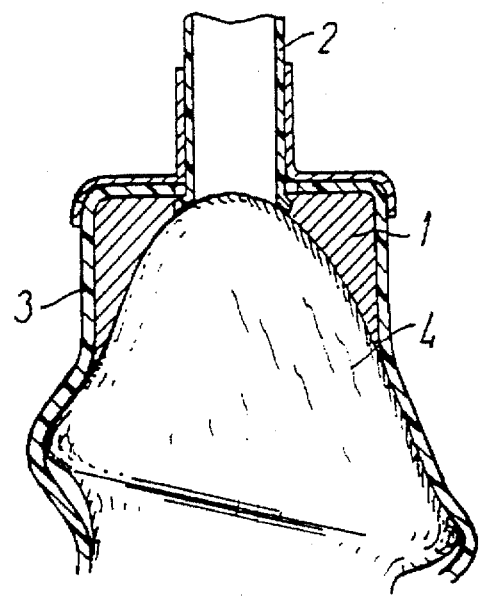

The example shown in FIGS. 1 and 2 of an external urinary catheter according to the invention comprises an inner catheter member 1 and a tubular discharge spout 2 intended for connection of the catheter with a hose, not shown, leading to a urine collection bag that may be of a known design.

The catheter member 1 and the discharge spout 2 are manufactured in one piece, e.g. by injection moulding of thermoplastic elastomeric material.

The catheter member 1, which as shown in FIG. 2 in the state of use is intended to be placed under the foreskin 3 in contact with the head or glans 4 of penis, has in the embodiment shown such a short axial extent, e.g. 5 to 35 mm, that in use it only covers the extreme portion of glans outside the point where glans has its largest diameter.

It thereby prevents the catheter member in the state of use being placed with its end edge 5 against the sensitive skin band between glans and foreskin.

At the transition to the discharge spout 2, the in itself elastically resilient catheter element 1 may, as shown, be designed with such a form stability that in use it preserves its outer shape at the place where the catheter member is fastened by the extreme portion of the foreskin 3.

In the embodiment in FIGS. 1 and 2, the increased form stability at the transition between the catheter member 1 and the discharge spout 2 is obtained in a simple manner in that the catheter member 1 is designed with an increased wall thickness in this local area.

The illustrated catheter member 1 is thus designed with an almost bowl-shaped profile, where a substantially plane outer surface 6 is provided about the discharge spout 2 substantially perpendicular to the discharge spout 2, whereas the side wall of the bowl-shaped profile is formed by a skirt portion 7, which joins the outer surface 6 via a shoulder-like ledge 8.

The internal side of the catheter member 1 constitutes an arched bowl-shaped bottom face 9 fitting to the shape of the extreme portion of glans 4.

The application is effected in that the catheter member 1 with the foreskin 3 retracted is placed against glans 4, the discharge spout being placed opposite the mouth of urethra, after which the foreskin 3 is passed out and around the catheter member 1 and fastens this in that the slightly stretched elastic foreskin presses against the outer surface 6.

According to the invention, there is used an outer holder member 10 to obtain an additionally secure fastening of the catheter member, said holder member being manufactured as a separate member with a tubular part 11 enveloping the discharge spout 2 but can be displaced axially thereon, possibly in connection with a backstop in the discharge spout 2, thereby diminishing the outer diameter thereof.

In connection with the spout-shaped part 11, the holder member 10 in the embodiment in FIGS. 1 and 2 has a substantially bowl-shaped profile 12 having a substantially uniform wall thickness.

The holder member 10 may like the catheter member 1 be manufactured by injection moulding of a thermoplastic elastomer.

Upon application, after that the catheter member 1 has been placed against glans 4 in the above described manner the holder member 10 is pressed against the outside of the foreskin 3 after this has been passed up around the catheter member 1.

The design of the holder member 10 as a separate member that may be displaced on the discharge spout 2 entails the advantage that in case of a tensile load on the discharge spout 2, e.g. due to the weight of the urine collection bag in use, only a pull in the catheter member will be exerted, since the tensile load causes an elastic extension and thus a somewhat smaller diameter of the discharge spout 2, whereas the holder member 10 is less affected. The tensile load will thus entail an increased squeeze effect on the extreme portion of the foreskin 3.

The fastening principle may thus in a way be said to be load compensating.

FIGS. 3 to 7 show various alternative designs.

Figure 3:
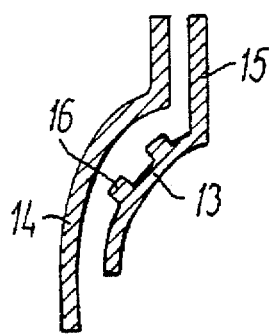
FIG. 3 shows a second embodiment of the invention.

In FIG. 3, the catheter member 13 and the holder member 14 are both formed with a bowl-shaped cross-section having a substantially uniform wall thickness. The enhanced form stability at the transition between the catheter member 13 and the discharge spout 15 is here obtained in that the catheter member 13 is provided with one or more circumferential ribs 16 on the outer side.

Figure 4:
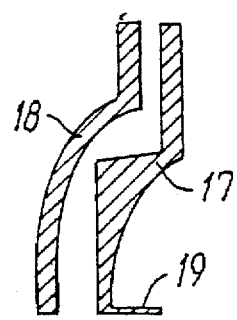
FIG. 4 shows a third embodiment of the invention.

In the embodiment in FIG. 4, in which the catheter member 17 and the holder member 18 have almost the same cross-sectional shape as in FIGS. 1 and 2, the catheter member is at its proximal end edge provided with an inwards extending, relatively soft sealing lip 19 which is particularly suited to give an improved sealing in case of more severe incontinence.

Figure 5:
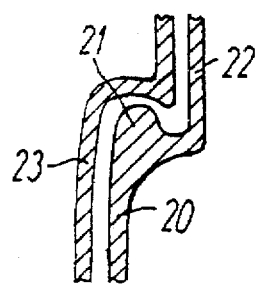
FIG. 5 shows a fourth embodiment of the invention.

In the embodiment in FIG. 5, the catheter member 20 is provided with a raised shoulder portion 21 at the transition to the discharge spout 22 and the cross-sectional shape of the holder member 23 is designed with a corresponding profile to obtain an additionally improved form stability and fastening ability.

Figure 6:
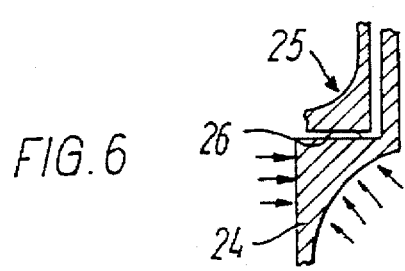
FIG. 6 shows a fifth embodiment of the invention.

In the embodiment in FIG. 6, in which the catheter member 24 substantially is designed as shown in FIGS. 1 and 2, the outer holder member 25 is designed as a relatively thin collar portion having a plane underside 26. It is thus not necessary that the holder member extends beyond and envelops the shoulder-like ledge on the catheter member.

Figure 7:
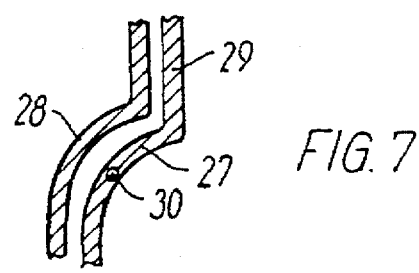
FIG. 7 shows a sixth embodiment of the invention.

Finally, FIG. 7 shows an embodiment, in which the catheter member 27 and the holder member 28 in principle are designed in the same manner as shown in FIG. 3 but in which the increased form stability at the transition to the discharge spout 29 is obtained by an embedded reinforcing or stiffening ring 30 which may be of an appropriate plastic material.

The invention is not limited to the illustrated design as described in the above of the catheter member with a quite short axial extent. The separate holder member according to the invention may thus also be used with a catheter member enveloping glans entirely such as it is known, e.g. in connection with the above GB patent application, even though such a design in most cases offers a reduced use comfort.

I claim:

1. An external urinary catheter for the relief of male urinary comprising an inner catheter comprising a catheter member (1, 13, 17, 20, 24, 27) and connected thereto a tubular discharge spout (2) for connection with a hose, said inner catheter being arrangeable in a position under the foreskin (3) of a penis in surface contact with the head (glans) (4) thereof, and a separate outer holder member (10) for circumferential engagement with the external side of the foreskin thereby to maintain the position of the inner catheter wherein the inner catheter has a short axial length of 5 to 35 mm so as to cover the extreme portion of glans (4) outside the point where glans has its largest diameter, the outer holder member (10) including a tubular spout part (11) axially displaceable around the discharge spout (2) of the inner catheter to permit axial displacement of the holder member towards a position of engagement with at least part of the external side of the foreskin opposite the underlying inner catheter.

2. An external urinary catheter according to claim 1, characterized in that said catheter member area of connection to the catheter discharge spout (2) is reinforced providing stability to the outer side of the inner catheter.

3. An external urinary catheter according to claim 2, characterized in that the catheter member (1) has a substantially plane abutment face (6) substantially perpendicular to the catheter discharge spout, said abutment face joining a short skirt portion (7) via a shoulder-like ledge (8).

4. An external urinary catheter according to claim 3, characterized in that the outer holder member (23,26) is provided with an inner face complimentary to the outer side of the inner catheter (20,24).

5. An external urinary catheter according to claim 3, characterized in that the outer holder member (25) includes a collar having a substantially plane side adapted to face the inner catheter (26).

6. An external urinary catheter according to claim 3, characterized in that the part of the outer holder member engaging the external side of the foreskin is substantially bowl-shaped.

7. An external urinary catheter according to claim 3, characterized in that the catheter member has at its proximal end edge an inwards extending, relatively soft sealing lip.

8. An external urinary catheter according to claim 2, characterized in that the inner catheter (13) has a circumferential rib (16) on the side facing the outer holder member.

9. An external urinary catheter according to claim 2, characterized in that the catheter (27) is substantially bowl-shaped and has an embedded circumferential stiffening ring (30).

10. An external urinary catheter according to claim 2, characterized in that the part of the outer holder member engaging the external side of the foreskin is substantially bowl-shaped.

11. An external urinary catheter according to claim 2, characterized in that the catheter member has at its proximal end edge an inwards extending, relatively soft sealing lip.

12. An external urinary catheter according to claim 1, characterized in that the part of the outer holder member (10, 14, 28) engaging the external side of the foreskin is substantially bowl-shaped.

13. An external urinary catheter according to claim 1, characterized in that the catheter member (17) has at its proximal end edge an inwards extending, relatively soft sealing lip (19).

* * * * *